US008419611B1

(12) United States Patent
Hatami

(10) Patent No.: US 8,419,611 B1

(45) Date of Patent: Apr. 16, 2013

(54) INTIMATE PLEASURE ENHANCING DEVICE

(76) Inventor: Jamshid Hatami, Valencia, CA (US)

( * ) Notice: Subject to any disclaimer, the term of this patent is extended or adjusted under 35 U.S.C. 154(b) by 874 days.

(21) Appl. No.: 12/586,603

(22) Filed: Sep. 24, 2009

Related U.S. Application Data

(60) Provisional application No. 61/194,152, filed on Sep. 25, 2008.

(51) Int. Cl.
*A61F 5/00* (2006.01)

(52) U.S. Cl.
USPC .......... 600/38

(58) Field of Classification Search .......... 600/38–41; 601/46, 51, 56–59, 61–62, 84
See application file for complete search history.

(56) References Cited

U.S. PATENT DOCUMENTS

2012/0123199 A1* 5/2012 Topolev .......... 600/38

* cited by examiner

*Primary Examiner* — John Lacyk

(74) *Attorney, Agent, or Firm* — Albert O. Cota

(57) ABSTRACT

An intimate pleasure enhancing device 10 (IPED 10) that is presented in four designs that function in combination with an elongated structure (12). The first design utilizes a rear ring (30) that is attached by a first spring (58) to a movable first stimulator (42) located adjacent the front end (14) of the structure (12). The second design utilizes a rear ring (30) and a front ring (82). The front ring (82) is attached to the rear ring (30) by the first spring (58) and a second spring (72). The third design utilizes a front ring (82) that has attached a resilient member (92) located across the first end (14) of the structure (12). The fourth design utilizes a magnetic displacement assembly (104) that utilizes a set of similar polarity permanent magnets (120,134) that cause a front ring (82) to move along the outer surface (18) of the elongated structure (12). The IPED (10) can also be designed to function with a spring roller (150) that allows the first ring (82) to roll over the elongated structure (12).

20 Claims, 3 Drawing Sheets

INTIMATE PLEASURE ENHANCING DEVICE

This application claims priority of Provisional Patent Application No. 61/194,152 filed on Sep. 25, 2008.

TECHNICAL FIELD

The invention generally pertains to intimate pleasure devices, and more particularly to an intimate pleasure device that is capable of enhancing and replicating a human effect when using the device.

BACKGROUND ART

There have existed devices, tools and toys that are designed to duplicate, facilitate or accentuate the human intimate experience.

One of the most well-known and widely used of these devices is a vibrator or dildo. Although both a vibrator and a dildo appear similar and share basic functionality, the main difference is that a vibrator utilizes power to provide a vibrating motion, and a dildo is typically non-powered.

Although these devices function adequately well, there is an inherent deficiency present in both as well as with human male organs. That deficiency results from the fact that both devices are taking the place of the human male organ. As a result, when using one of these devices, a person does not acquire an improved sensation over conventional human contact.

A percentage of females are stimulated by vaginal stimulation and others by clitoral stimulation. Presently there are no known devices or male organs that can stimulate both simultaneously and conveniently.

Obviously, if there was a way to stimulate both vaginal and clitoral experience simultaneously by a male human organ or when using one of these devices, the benefit would be substantial.

DISCLOSURE OF THE INVENTION

The invention disclosed herein is presented in multiple design configurations for an intimate pleasure enhancing device (IPED). Although there have long existed devices, accessories and toys that enhance or facilitate an intimate physical experience, many of these items lack the realism that is sought. One of the most popular intimate items is a tubular member that is commonly referred to as a vibrator or a dildo. A vibrator or dildo can be used by an individual or by partners, but unfortunately, regardless of the number of people using a vibrator or dildo, there exists a deficiency.

The instant invention addresses this deficiency by providing in its basic design, an elongated structure that has movably attached a ring. The ring functions as a stimulator and is attached to the elongated enclosure by means of a resilient member. When pressure is applied to the ring, the ring moves along the surface of the elongated structure. When the pressure is removed, the resilient member causes the ring to return to its initial position.

BEST MODE FOR CARRYING OUT THE INVENTION

Figure 1:
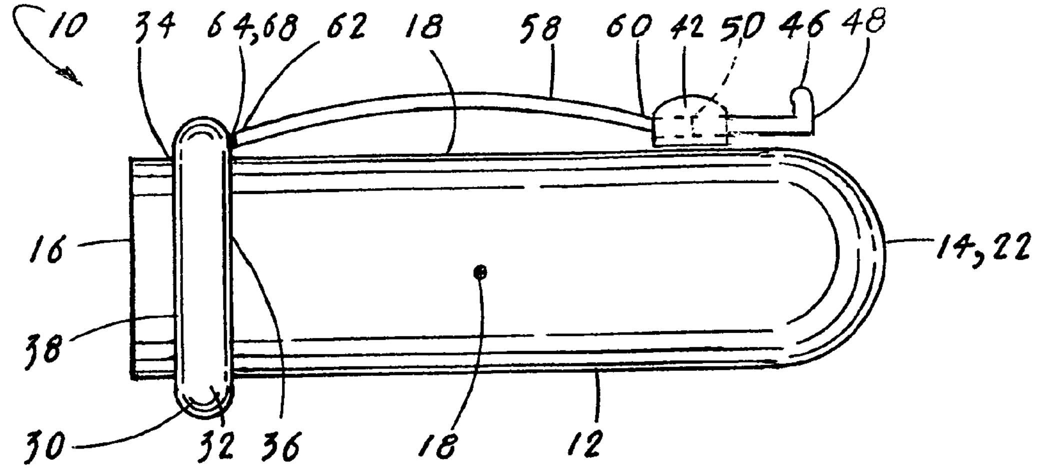
FIG. 1 is a side elevational view of an elongated structure having a rear ring that is connected to a first movable stimulator by means of a spring

The best mode for carrying out the invention is presented in terms that disclose a preferred embodiment of an intimate pleasure enhancing device 10 (IPED 10). The IPED 10 is further presented in four design configurations, as shown in FIGS. 1-9.

The first design configuration, as shown in FIGS. 1-5, is comprised of seven major elements: an elongated structure 12, a rear ring 30, a first stimulator 42, a second stimulator 46, a first spring 58, a second spring 72 and a third stimulator 80.

The elongated structure 12, which can consists of a male organ, has a front end 14, a rear end 16 and an outer surface 18 and can be produced from several materials including plastic, metal, wood, carbon fiber, glass or rubber. As shown in FIGS. 1-5, the front end 14 of the elongated structure 12 can have a shape that is selected from the group consisting of radiused 22, flat 24, pointed 26 and multi-faceted 28.

Figure 2:
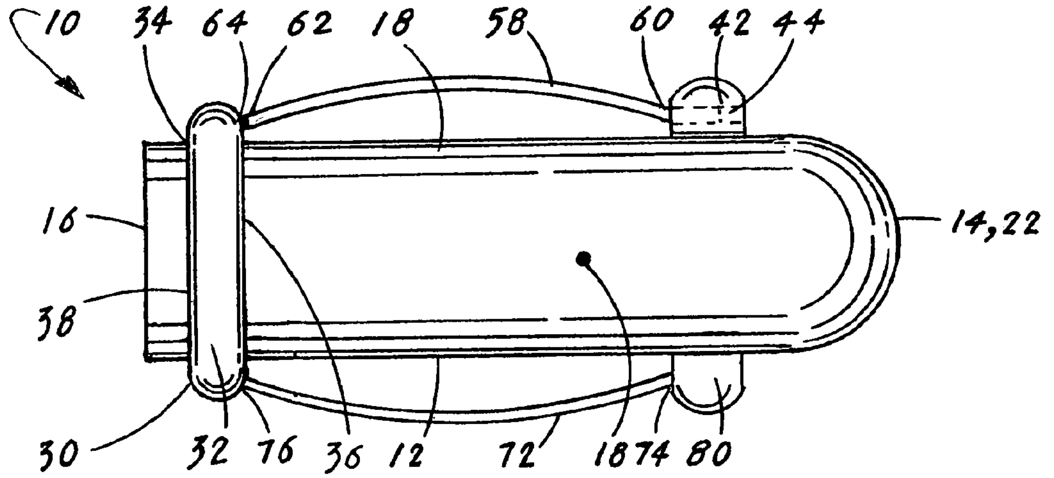
FIG. 2 is a side elevational view of an elongated structure having a rear ring that is attached to a pair of movable stimulators by a pair of springs.
Figures 3, 4, 5:
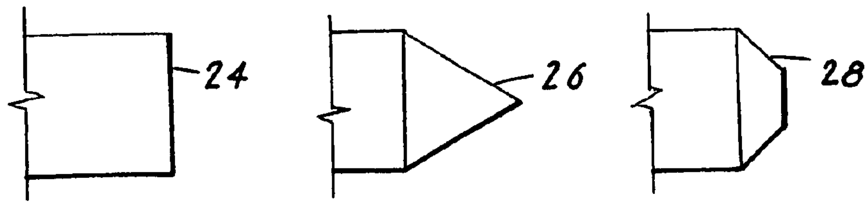
FIG. 3 is a partial side elevational view of an elongated structure having a flat front end.
FIG. 4 is a partial side elevational view of an elongated structure having a pointed front end.
FIG. 5 is a partial side elevational view of an elongated structure having a multi-faceted front end.

The rear ring 30, as shown in FIGS. 1, 2 and 3, has an outer edge 32, an opening 34, a front surface 36 and a rear surface 38. The opening 34 is dimensioned to be inserted over the outer surface 18 of the elongated structure 12. The rear ring 30 is preferably rigidly attached by an attachment means 64 to the outer surface 18 and adjacent to the rear end 16 of the elongated structure 12. The ring attachment means 64 can consist of a clip 66, an adhesive 68 or a pin 70. The rear ring 30 can also be designed to be movably attached to the elongated structure 12.

Three stimulators are disclosed. The first stimulator 42, as shown in FIGS. 1 and 2, has a longitudinal bore 44 and is movably located on the outer surface 18 and adjacent to the front end 14 of the elongated structure 12. The first spring 58 extends along the outer surface 18 of the elongated structure 12 and has a first end 60 and a second end 62. The first end 60 is captively inserted into the longitudinal bore 44 on the first stimulator 42. The second end 62 is rigidly attached by the attachment means 64 to the front surface 36 and adjacent to the outer edge 32 of the rear ring 30.

When rearward pressure is applied to the first stimulator 42, the stimulator 42 overcomes the force applied by the first spring 58 and slides long the outer surface 18 of the elongated structure 12. Likewise, when rearward pressure is no longer applied the first stimulator 42 returns to the stimulator's initial position.

The second stimulator 46, as shown in FIG. 1, has a front end 48 and a rear end 50. The rear end 50 is inserted into the longitudinal bore 44 located on the first stimulator 42 and the front end extends outward from the first stimulator 42. The second stimulator 46 can be straight, located parallel to the outer surface 18 of the elongated structure 12 and has a selectable length. Alternatively, the outward-extending front end 48 of the second stimulator 46, as also shown in FIG. 1, can be angled at a selectable length, as viewed from the outer surface 18 of the elongated structure 12.

The first design of the IPED 10, as shown in FIG. 2, can also be designed to include a second spring 72. The second spring 72 is angularly displaced from the first spring 58 and extends along the outer surface 18 of the elongated structure 12. The second spring 72 also has a first end 74 and a second end 76. The first end 74 is attached to a third stimulator 80 that is movably located adjacent to the front end 14 of the elongated structure 12. The second end 76 of the second spring 72 is attached by the attachment means 64 to the front surface 36 and adjacent to the outer edge 32 of the rear ring 30.

Figure 6:
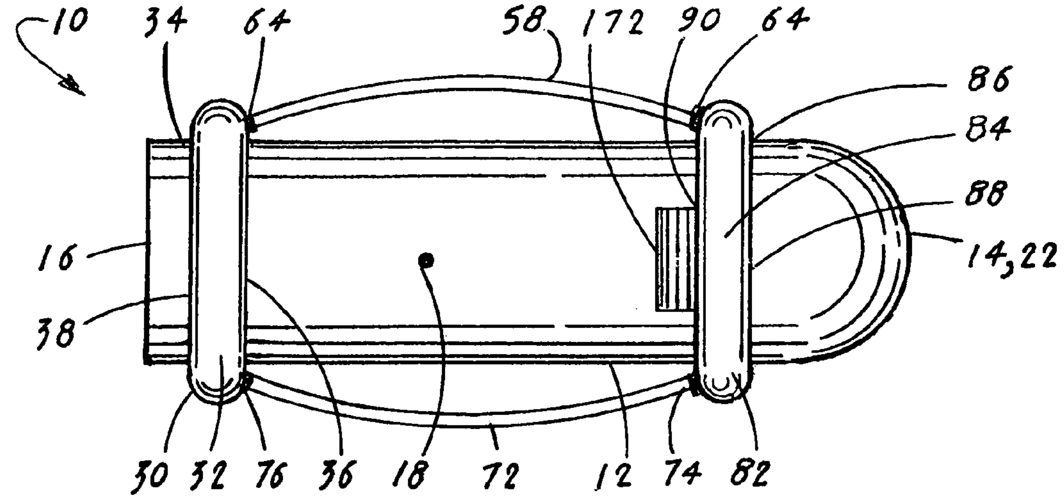
FIG. 6 is a side elevational view of an elongated structure having a rear ring and a front ring that are connected together by a pair of springs.

The second design of the IPED 10, as shown in FIG. 6, is comprised of an elongated structure 12, a rear ring 30, a front ring 82, a first spring 58 and a second spring 72.

The elongated structure 12 has a front end 14, a rear end 16 and an outer surface 18, and is similarly designed and produced as in the first design of the IPED 10.

The rear ring 30 is similar to the rear ring 30 used in the first design and includes an outer edge 32, an opening 34, a front surface 36 and a rear surface 38. The opening 34 of the rear ring 30 is dimensioned to be inserted over the outer surface 18 of the elongated structure 12 and is located adjacent to the rear end 16 of the elongated structure 12. The rear ring 30 can be rigidly attached or movably attached by the attachment means 64 such as an adhesive 68.

The front ring 82, as shown in FIG. 6, also has an outer edge 84, an opening 86, a front surface 88 and a rear surface 90. The opening 86 of the front ring 82 is dimensioned to allow the front ring 82 to be slideably inserted over and adjacent to the front end 14 of the elongated structure 12. The two rings 30,82 are connected together respectively by a first spring 58 and a second spring 72.

The first spring 58 has a first end 60 that is attached to the rear surface 90 and adjacent to the outer edge 84 of the front ring 82. The second end 62 is attached to the front surface 36 and adjacent to the outer edge 32 of the rear ring 30. When rearward pressure is applied to the front ring 82 it moves along the upper surface 18 of the elongated structure 12, wherein when the rearward pressure is no longer applied, the front ring 82 slides forward and returns to its initial spring-biased position.

As shown in FIG. 6, the second design can be designed to include at least a second spring 72 that is angularly displaced from the first spring 58 and that extends along the outer surface 18 of the elongated structure 12. The at least second spring 72 comprises a first end 74 that is attached to the rear surface 90 and adjacent to the outer edge 84 of the front ring 82. The second end 76 is attached to the front surface 36 and adjacent to the outer edge 32 of the rear ring 30.

Figure 7:
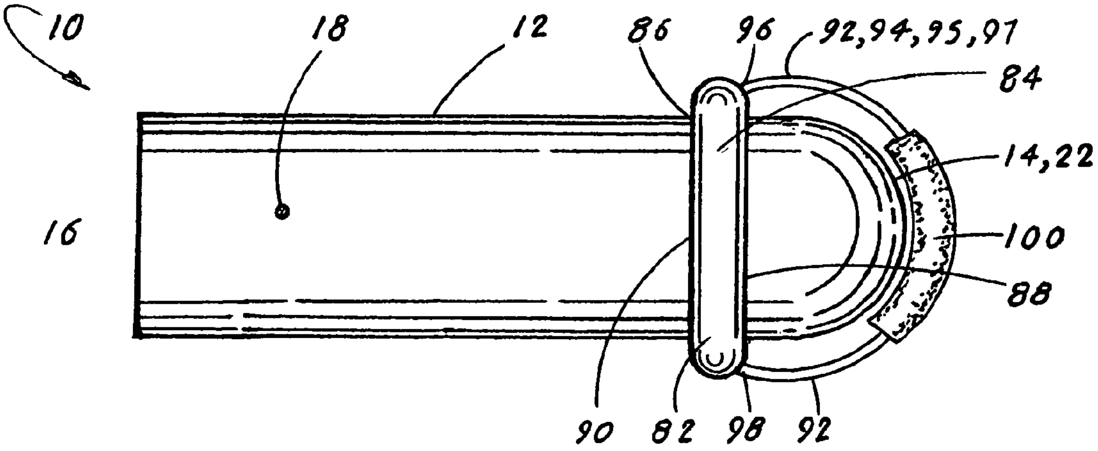
FIG. 7 is a side elevational view of an elongated structure having a front ring member that is connected by a front padded spring.

The third design of the IPED 10, as shown in FIG. 7, is comprised of an elongated structure 12, a front ring 82, a resilient member 92 and a pad 100 that can be designed to be removable.

The elongated structure 12 used in the third design also has a front end 14, a rear end 16 and an outer surface 18.

The front ring 82 has an outer edge 84, an opening 86, a front surface 88 and a rear surface 90. The front ring 82 is dimensioned to be slidably inserted over the outer surface 18 and adjacent to the front end 14 of the elongated structure 12.

The resilient member 92, can consist of an elastic band 94, a spring 95 or an elastic membrane 97. The resilient member 92 has a first end 96 and a second end 98. The first end 96 is attached by the attachment means 64 to the front surface 88 and adjacent to the outer edge 84 of the front ring 82, and the second end 98 of the resilient member 92 is anguarly displaced from the first end 96 of the resilient member 92 and is attached by the attachment means 64 to the front surface 88 and adjacent to the outer edge 84 of the front ring 82.

To add comfort to the second design of the IPED 10, the removable soft pad 100 is utilized. The pad 100 is inserted over or under the resilient member 92 between the first end 96 and the second end 98 of the resilient member 92.

Figure 8:
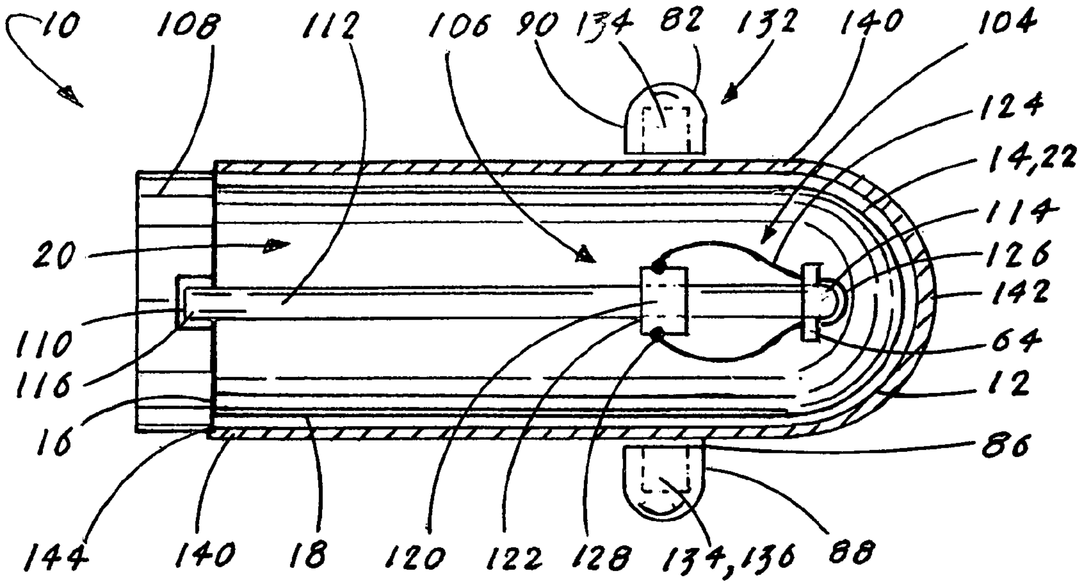
FIG. 8 is a side elevational and partial cross-sectional view of a magnetic displacement assembly that is utilized to displace a front ring.

The fourth design of the IPED 10, as shown in FIG. 8, is comprised of a magnetic displacement assembly 104 that consists of an internal unit 106 and an external unit 132.

The internal unit 106 is dimensioned to be located within a cavity 20 located on the elongated structure 12 and is comprised of a cap 108, a rod 112, a first permanent magnet 120, and a resilient member 124 which can consist of an elastic band, a spring or the like.

The cap 108, as shown in FIG. 8, has a centered rod cavity 110 and is preferably designed to include threads that allow the cap 108 to be removably attached to the rear end 16 of the elongated structure 12. The rod 112 has a front end 114 and a rear end 116. The rear end 116 is centrally positioned and attached when the rod 112 is inserted into the rod cavity 110, as shown in FIG. 8.

The first permanent magnet 120 has a bore 122 that is frictionally inserted over the rod 112 and is located proximate to the front end 14 of the elongated structure 12. The resilient member 124 has a front side 126 and a rear side 128. The front side 126 is attached by an attachment means 64, that can consist of a clip or a washer to the front end 114 of the rod 112 and the rear side 128 is attached to the first permanent magnet 120 by an attachment means 64. The resilient member 124 is designed to maintain the first permanent magnet 120 in an initial position.

The external unit 132, as also shown in FIG. 8, is comprised of a front ring 82 and a second permanent magnet 134. The front ring 82 has an outer edge 84, a front surface 88, a rear surface 90 and a central opening 86 that is dimensioned to allow the front ring 82 to move along the outer surface 18 of the elongated structure 12.

The second permanent magnet 134 is substantially located along the inner edge of the opening 86 on the front ring 82 and has a polarity that is similar to the polarity of the first permanent magnet 120. Under a non-use mode, the front ring 82 is initially located over the first permanent magnet 120, wherein the magnetic repulsion provided by the two magnets causes the front ring 82 to remain in its initial position each time the front ring 82 is placed on the elongated structure 12.

The second permanent magnetic 134 is preferably comprised of a ring magnet 136 that is attached to the inner surface of the opening 86 on the front ring 82. The second permanent magnet 134 can also be comprised of at least one magnet 134 that is attached to the inner surface of the opening 86 on the front ring 82. The facing magnetic surfaces of the first permanent magnet 120 and the second permanent magnet 134 can be angled (not shown) to control the direction and force applied by the two magnets 120,134.

To further enhance the aesthetic of the IPED 10, an outer enclosure 140 that is made of a non-magnetic material and having a closed front end 142 and a rear cavity 144 can be utilized. The enclosure 140 is dimensioned to be placed over the outer surface 18 of the elongated structure 12, as shown in FIG. 8.

Figure 9:
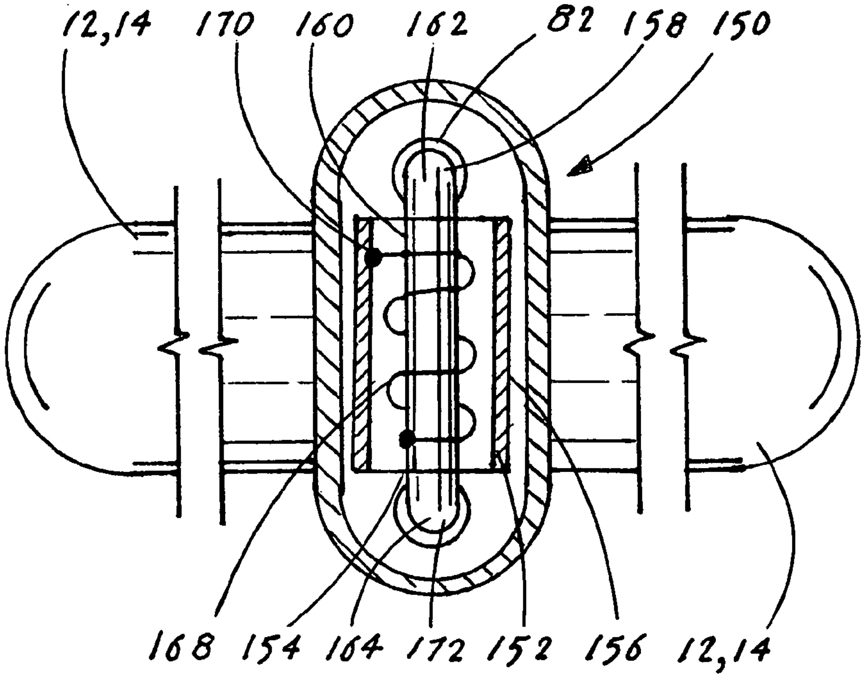
FIG. 9 is a side elevational and partial cross-sectional view of a spring roller that is utilized to displace a front ring.

To control the forward and rearward displacement of the front ring 82, as disclosed for the various designs, a spring roller 150, as shown in FIG. 9 can be utilized. The spring roller 150 is comprised of a spindle 152, a spindle mounting rod 158 and a spring 168.

The spindle 152 has a central bore 154 and an outer surface 156 that is spaced apart from the inner wall of the elongated structure 12. The spindle mounting rod 158 which is rotatably inserted into the central bore 154, has an outer surface 160, a first end 162 that is rigidly attached to one side of said front ring 82 and a second end 164 that is rigidly attached to a second side of the front ring 82 and as shown in FIG. 9.

The spring 168, which is wound around the outer surface 160 of the rod 158 has a first end 170 that is attached to the spindle 152 and a second end 172 that is attached to the rod 158. When rearward pressure is applied to the front ring 82, the spring roller 150 causes the front ring 82 to roll along the outer surface 18 of the elongated structure 12. When the rearward pressure is no longer applied the spring 158 causes the spring roller 150 to return the front ring 82 to its initial position.

To increase the utility of the IPED 10 a compact vibrator 180, as shown in FIG. 6, can be utilized. The vibrator 180 is typically attached by an attachment means 64 to either the front surface 88 or the rear surface 90 of the front ring 30. A vibrator 180 is shown attached to the rear surface 90 of the front ring 82 in FIG. 6.

While the invention has been described in detail and pictorially shown in the accompanying drawings it is not to be limited to such details, since many changes and modifications may be made to the invention without departing from the spirit and the scope thereof. For example, dual stimulators which are disclosed in the prior art, can be lengthened and used with the instant invention. Hence, it is described to cover any and all modifications and forms which may come within the language and scope of the claims.

| | |
|---|---|
| 10 | Intimate Pleasure Enhancing Device |
| 12 | Elongated Structure |
| 14 | Front End |
| 16 | Rear End |
| 18 | Outer Surface |
| 20 | Cavity |
| 22 | Radiused |
| 24 | Flat |
| 26 | Pointed |
| 28 | Multi-Faceted |
| 30 | Rear Ring |
| 32 | Outer Edge |
| 34 | Opening |
| 36 | Front Surface |
| 38 | Rear Surface |
| 40 | |
| 42 | First Stimulator |
| 44 | Longitudinal Bore |
| 46 | Second Stimulator |
| 48 | Front End |
| 50 | Rear End |
| 52 | |
| 54 | |
| 56 | |
| 58 | First Spring |
| 60 | First End |
| 62 | Second End |
| 64 | Attachment Means |
| 66 | Clip |
| 68 | Adhesive |
| 70 | Pin |
| 72 | Second Spring |
| 74 | First End |
| 76 | Second End |
| 78 | |
| 80 | Third Stimulator |

-continued

| | |
|---|---|
| 82 | Front Ring |
| 84 | Outer Edge |
| 86 | Opening |
| 88 | Front Surface |
| 90 | Rear Surface |
| 92 | Resilient Member |
| 94 | Elastic Band |
| 95 | Spring |
| 96 | First End |
| 97 | Elastic Membrane |
| 98 | Second End |
| 100 | Removable Pad |
| 102 | |
| 104 | Magnetic Displacement Assem. |
| 106 | Internal Unit |
| 108 | Cap |
| 110 | Rod Cavity |
| 112 | Rod |
| 114 | Front End |
| 116 | Rear End |
| 118 | |
| 120 | First Permanent Magnet |
| 122 | Bore |
| 124 | Resilient Member |
| 126 | Front Side |
| 128 | Rear Side |
| 130 | |
| 132 | External Unit |
| 134 | Second Permanent Magnet |
| 136 | Ring Magnet |
| 138 | |
| 140 | Outer Enclosure |
| 142 | Closed Front End |
| 144 | Rear Cavity |
| 146 | |
| 148 | |
| 150 | Spring Roller |
| 152 | Spindle |
| 154 | Central Bore |
| 156 | Outer Surface |
| 158 | Spindle Mounting Rod |
| 160 | Outer Surface |
| 162 | First End |
| 164 | Second End |
| 166 | |
| 168 | Spring |
| 170 | First End |
| 172 | Second End |
| 174 | |
| 176 | |
| 178 | |
| 180 | Vibrator |

The invention claimed is:

1. An intimate pleasure enhancing device (IPED) comprising:

a) an elongated structure having a front end, a rear end and an outer surface, b) a rear ring having an outer edge, an opening, a front surface and a rear surface, wherein the opening is inserted over and is movably or rigidly attached by an attachment means to the outer surface and adjacent to the rear end of said elongated structure, c) a first stimulator having a longitudinal bore, and that is movably located on the outer surface and adjacent to the front end of said elongated structure, d) a first spring that extends along the outer surface of said elongated structure, said first spring having:

(1) a first end that is captively inserted into the longitudinal bore on said first stimulator, and (2) a second end that is rigidly attached by an attachment means, to the front surface and adjacent to the outer edge of said rear ring, wherein when rearward pressure is applied to said first stimulator, the first stimulator overcomes the force applied by said first spring and moves along the outer surface of said elongated structure.

2. The IPED as specified in claim 1 wherein the front end of said elongated structure has a shape that is selected from the group consisting of radiused, flat, pointed and multi-faceted.

3. The IPED as specified in claim 2 further comprising a second stimulator having a front end and a rear end, wherein the rear end is inserted into the bore on said first stimulator, and the front end extends outward from said first stimulator.

4. The IPED as specified in claim 2 wherein said second stimulator is straight and is located parallel to the outer surface of said elongated structure and can have a selectable length.

5. The IPED as specified in claim 2 wherein the outward-extending front end of said second stimulator is angled as viewed from the outer surface of said elongated structure and can have a selectable length.

6. The IPED as specified in claim 1 wherein said means for attaching the second end of said first spring to said rear ring comprises a clip or an adhesive.

7. The IPED as specified in claim 2 further comprising at least an additional second spring that is angularly displaced from the first spring and that extends along the outer surface of said elongated structure, said second spring having:

a) a first end that is attached to a third stimulator that is movably located adjacent to the front end of said elongated protrusion, and b) a second end that is attached by an attachment means, to the front surface and adjacent to the outer edge of said rear ring.

8. An intimate pleasure enhancing device (IPED) comprising:

a) an elongated structure having a front end, a rear end and an outer surface, b) a rear ring having an outer edge, an opening, a front surface and a rear surface, wherein said rear ring is inserted over the outer surface and is located adjacent to the rear end of said elongated structure, c) a front ring having an outer edge, an opening, a front surface and a rear surface, wherein said front ring is slidably inserted over and adjacent to the front end of said elongated structure, d) a first spring having:

(1) a first end that is attached to the rear surface and adjacent to the outer edge of said front ring, and (2) a second end that is attached to the front surface and adjacent to the outer edge of said rear ring, wherein when rearward pressure is applied to said front ring, the front ring moves along the upper surface of said elongated structure, wherein when the rearward pressure is no longer applied, said front ring returns to an initial spring-biased position.

9. The IPED as specified in claim 8 further comprising at least a second spring that is angularly displaced from the first spring and that extends along the outer surface of said elongated structure, said at least second spring comprises:

a) a first end that is attached to the rear surface and adjacent to the outer edge of said front ring, and b) a second end that is attached to the front surface and adjacent to the outer edge of said rear ring.

10. An intimate pleasure enhancing device (IPED) comprising:

a) an elongated structure having a front end, a rear end and an outer surface, b) a front ring having an outer edge, an opening, a front surface and a rear surface, wherein said front ring is slidably inserted over the outer surface and adjacent to the front end of said elongated structure, and c) a resilient member having a first end and a second end, wherein the first end is attached by an attachment means to the front surface and adjacent to the outer edge of said front ring, and the second end of said resilient member is angularly displaced from the first end of said resilient member and is attached by an attachment means to the front surface and adjacent to the outer edge of said front ring.

11. The IPED as specified in claim 10 further comprising a removable pad that is inserted over said resilient member between the first end and the second end of said resilient member.

12. An intimate pleasure enhancing device (IPED) comprising:

A. an elongated structure having a front end, a rear end, an outer surface and a cavity, B. a magnetic displacement assembly comprising:

(1) an internal unit that is located within the elongated structure cavity and comprising:

(a) a cap having a centered rod cavity, wherein the cap is removably attached to the rear end of said elongated structure, (b) a rod having a front end and a rear end, wherein the rear end is centrally positioned and attached when inserted into the rod cavity, (c) a first permanent magnet having a bore that is inserted over said rod and that is located proximate to the front end of said elongated structure, and (d) a resilient member having a front side and a rear side, wherein the front side is attached by an attachment means to the first end of said rod and the rear side is attached to said first permanent magnet by an attachment means, wherein said resilient member maintains said first permanent magnet in an initial first position, (2) an external unit comprising:

(a) a front ring having an outer edge, a front surface, a rear surface and an opening that is dimensioned to allow said front ring to move along the outer surface of said elongated structure, and (b) a second permanent magnet located along the inner edge of the opening on said front ring and having a similar polarity as that of said first permanent magnet, wherein under a non-use mode, said front ring is initially located over the first permanent magnet, wherein the magnetic repulsion provided by the two magnets in combination with the resilient member, causes said front ring to repeatably return to its initial position each time said front ring is displaced by a rearward applied force.

13. The IPED as specified in claim 12 wherein said second permanent magnet is comprised of a ring magnet that is attached to the inner surface of the opening on said front ring.

14. The IPED as specified in claim 12 wherein said second permanent magnet is comprised of at least one magnet that is attached to the inner surface of the opening on said front ring.

15. The IPED as specified in claim 12 wherein the complimentary magnetic surfaces of said first permanent magnet and said second permanent magnet are angled to control the direction and force applied by said magnets.

16. The IPED as specified in claim 12 further comprising an outer enclosure made of a non-magnetic material and having a closed front end and a rear cavity that is dimensioned to accept and retain said inner unit.

17. The IPED as specified in claim 10 wherein said resilient member is selected from the group consisting of an elastic band, a spring and at least one spring roller.

18. The IPED as specified in claim 17 wherein said at least one spring roller comprises:

a) a spindle having a central bore and an outer surface, b) a spindle mounting rod rotatably inserted into the central bore, wherein said rod has an outer surface, a first end that is rigidly attached to one side of said front ring, and a second end that is rigidly attached to a second side of said front ring, and c) a spring wound around the outer surface of said rod, wherein said spring has a first end that is attached to said spindle and a second end that is attached to said rod, wherein when rearward pressure is applied to said front ring said spring roller causes said front ring to roll along the outer surface of said elongated structure, wherein when the rearward pressure is no longer applied, said spring causes said spring roller to return said front ring to its initial position.

19. The IPED as specified in claim 8 further comprising a vibrator that is attached by an attachment means to either the front surface or the rear surface of said front or rear rings.

20. The IPED as specified in claim 2 wherein said elongated structure, said front ring and said rear ring are made of a material that is selected from the group consisting of plastic, metal, wood, carbon fiber, glass and rubber.

* * * * *